United States Patent [19]

Hansen et al.

[11] Patent Number: 4,565,783
[45] Date of Patent: Jan. 21, 1986

[54] DRY CULTURE MEDIA

[75] Inventors: Paul E. Hansen; Robert L. Nelson, both of St. Paul, Minn.

[73] Assignee: Minnesota Mining and Manufacturing Company, St. Paul, Minn.

[21] Appl. No.: 338,559

[22] Filed: Jan. 11, 1982

Related U.S. Application Data

[63] Continuation-in-part of Ser. No. 228,893, Jan. 27, 1981, abandoned.

[51] Int. Cl.$^4$ .......................... C12M 1/16; C12Q 1/24
[52] U.S. Cl. ...................................... 435/299; 435/30; 435/805
[58] Field of Search ..................... 435/30, 34, 299, 805

[56] References Cited

U.S. PATENT DOCUMENTS

| | | | |
|---|---|---|---|
| 2,761,813 | 9/1956 | Goetz | 195/80 |
| 2,954,327 | 9/1960 | Kanz | 195/139 |
| 3,360,440 | 12/1967 | Haab et al. | 195/100 |
| 3,416,998 | 12/1968 | Streitfeld | 195/103.5 |
| 3,551,295 | 12/1970 | Dyer | 195/103.5 |
| 3,713,985 | 1/1973 | Astle | 435/301 X |
| 3,751,341 | 8/1973 | Seitz et al. | 195/139 |
| 3,785,930 | 1/1974 | Ellis | 195/127 |
| 3,802,842 | 4/1974 | Lange et al. | 195/103.5 |
| 3,814,670 | 6/1974 | Freake et al. | 435/34 X |
| 3,843,456 | 10/1974 | Haden et al. | 195/139 |
| 3,881,993 | 5/1975 | Freake et al. | 195/139 |
| 3,954,563 | 5/1976 | Mennen | 195/127 |
| 4,077,845 | 3/1978 | Johnson | 195/103.5 |
| 4,241,186 | 12/1980 | Roth | 435/243 |
| 4,250,256 | 2/1981 | Wielinger et al. | 435/32 |

Primary Examiner—Robert J. Warden
Assistant Examiner—Randall E. Deck
Attorney, Agent, or Firm—Donald M. Sell; James A. Smith; Robert W. Sprague

[57] ABSTRACT

A device for culturing microorganisms is described comprising a body member comprising a self-supporting, water-proof substrate; a layer of adhesive coated on the substrate, the adhesive being non-inhibitory to the growth of microorganisms; and a cold-water-soluble powder adhered uniformly to the surface of the adhesive, the powder comprising a gelling agent and/or nutrients for growing microorganisms. Another device is described comprising a body member comprising a self-supporting, water-proof substrate; a coating coated directly on the substrate, the coating being substantially water-free and consisting essentially of a cold-water-reconstitutable material comprising a gelling agent and/or nutrients for growing microorganisms; and a cover sheet releasably adhered to the bottom member, the cover sheet being substantially impermeable to bacteria and water vapor. The devices are activated by the addition of water or an aqueous test sample.

33 Claims, 4 Drawing Figures

DRY CULTURE MEDIA

CROSS REFERENCE TO RELATED APPLICATION

This application is a continuation-in-part of copending U.S. application Ser. No. 228,893, which was filed on Jan. 27, 1981 and is now abandoned.

FIELD OF THE INVENTION

This invention relates to a device for culturing microorganisms. In particular, it relates to a device containing a culture medium in a form which is cold-water-reconstitutable. When contacted with water, the medium forms a substantially homogeneous medium without mixing.

BACKGROUND ART

Media for culturing bacteria are generally prepared by dispersing a solidifying agent in an aqueous solution containing nutrients and other ingredients necessary for the growth of specific microorganisms. Unfortunately, use of conventional solidifying agents is often inconvenient for the end-user. For example, when carrying out standard "plate count" or "pour plate" methods to determine the number of microorganisms in a liquid sample such as water or milk, the use of conventional agar medium is particularly inconvenient and time-consuming. The agar medium, which has generally been prepared in bulk and sterilized ahead of time, must be melted in boiling water or by exposure to flowing steam. The hot agar must then be carefully cooled to approximately 45° C. prior to pouring into petri dishes. A series of dilutions of the test sample is then prepared and an aliquot of each dilution is placed in a petri dish. The cooled, but still liquified, agar medium is then poured into each dish, mixed with the aliquot of test sample, swirled to mix and allowed to solidify. After incubation, the number of colonies growing in each dish are counted by visual inspection. In this manner the number of microorganisms or colony-forming units present in the test sample can be determined.

It is apparent from the foregoing description that a simpler method of obtaining standard plate counts is desirable, particularly one that eliminates the need for the end-user to melt and cool the agar medium and pour it into the petri dishes.

The prior art has provided several gelling agents for microbiological growth media which are rehydratable at room temperature. For example, U.S. Pat. No. 3,046,201 suggests the use of certain polyacrylamides as gelling agents. U.S. Pat. No. 3,360,440 describes a microbiological medium in which the gelling agent is a cold-water-soluble modified cellulose. The aforementioned gelling agents are prepared by special processes involving expensive lyophilization procedures to increase the surface area of the dry powder to render it more easily rehydrated. When rehydrated, mixing is generally required to obtain a homogeneous gel.

U.S. Pat. No. 3,881,993 describes a device for assaying liquid specimens for microorganisms. One embodiment of the device comprises filter paper which is impregnated with a gelling agent and nutrients for growing microorganisms and which is adhered to a film by means of an adhesive layer. This embodiment suffers from the disadvantage that it is generally only semi-quantitative, due possibly to the presence of the filter paper. It is believed the filter paper is not suitably transparent and that it therefore renders counting of bacterial colonies difficult. Also, presence of the filter paper renders isolation of individual bacterial colonies impractical.

SUMMARY OF THE INVENTION

The present invention provides a preferred device for growing microorganisms, comprising: a bottom member comprising a self-supporting water-proof substrate having upper and lower surfaces; a layer of adhesive coated on the upper surface of the substrate, the adhesive being noninhibitory to the growth of microorganisms; and a coating of cold-water-soluble powder adhered uniformly to the surface of the adhesive, the powder comprising at least one ingredient selected from the group consisting of a gelling agent, one or more nutrients for growing microorganisms and a mixture thereof. Preferably, the device further comprises a cover sheet releasably adhered to at least a portion of the body member to prevent contamination of the device during storage and incubation.

The present invention also provides a device for growing microorganisms, comprising: a bottom member comprising a self-supporting, water-proof substrate having upper and lower surfaces with a coating adhered to at least a portion of the upper surface, the coating being substantially water-free and consisting essentially of a cold-water-reconstitutable material comprising at least one ingredient selected from the group consisting of a gelling agent, one or more nutrients for growing microorganisms, and a mixture thereof; and a cover sheet releasably adhered to at least a portion of the bottom member, the cover sheet being substantially impermeable to bacteria and water vapor.

If a gelling agent is present in the coating of cold-water-reconstitutable material (the cold-water-soluble powder in the preferred device), it is preferably present in an amount sufficient to form a substantially transparent gel having a Brookfield viscosity of at least 1500 cps. In the preferred embodiment, a dye is also included in the coating of cold-water-reconstitutable material. The dye is soluble in the aqueous medium so that it can react with the growing microorganisms and enables better visualization of the bacterial colonies.

The means for covering the substrate to prevent contamination during incubation is preferably a sheet attached in hinge-like fashion to one end of the body member. The cover sheet is simply peeled back, and the liquid sample placed on the substrate. The cover sheet is then returned to its original position thereby sealing in the gelled medium. The cover sheet is preferably transparent to allow the bacterial colonies to be seen. Optionally, the surface of the cover sheet contacting the substrate may have a coating of cold-water-reconstitutable material adhered thereto, that coating containing a gelling agent and/or nutrients for growing microorganisms. The materials used to form the cover sheet may be conveniently selected to obtain the desired permeability to gases such as oxygen.

When a predetermined amount of water or other aqueous test sample is placed on the substrate in contact with the coating of cold-water-reconstitutable material, the gelling agent preferably contained in that coating immediately hydrates in the sample along with the other dry ingredients adhered to the substrate and forms a gelled medium. No mixing is required. There is no need for the end-user to heat the medium or otherwise treat it to obtain a homogeneous gel.

The devices of the invention provide a marked improvement over prior art devices and techniques for carrying out standard pour plate methods as well as other microbiological testing. The coatings of medium of the devices of the present invention do not contain matrixes which would adversely affect one's ability to visualize and isolate bacterial colonies. Not only will the medium provided by the device allow enumeration of the bacterial colonies growing in the medium, but the colonies may be easily isolated for further testing in the same manner as bacterial colonies growing on conventional agar medium in a petri dish. The devices have the added feature of being much more compact and light-weight than petri dishes and take up less space in the laboratory. Furthermore, the devices are completely disposable allowing for safer and more rapid clean-up after use. The preferred devices of the present invention (i.e., those comprising a cold-water-soluble powder which comprises a gelling agent) provide results comparable to those provided by conventional pour plates.

DESCRIPTION OF THE DRAWINGS

The invention may be further illustrated by reference to the accompanying drawings wherein:

FIGS. 1 and 4 illustrate a preferred device in accordance with the present invention. The microbiological growing device 10 includes a body member comprising a self-supporting water-proof substrate 12 having upper and lower surfaces. Substrate 12 is preferably a relatively stiff film of a material such as polyester, polypropylene or polystyrene which will not absorb or otherwise be affected by water. Polyester films approximately 0.004 to 0.007 inch thick, polypropylene films approximately 0.004 to 0.008 inch thick and polystyrene films approximately 0.015 inch thick have been found to work well. Other suitable substrates include paper with a polyethylene or other water-proof coating. An example of a suitable polyethylene-coated paper substrate is "Schoeller Type MIL" photoprint paper (commercially available from Schoeller Pulaski, New York). The substrate 12 may be either transparent or opaque, depending on whether one wishes to view bacterial colonies through the substrate. To facilitate the counting of bacterial colonies, the substrate 12 preferably has a square grid pattern printed thereon as shown in FIG. 4.

Figure 1:
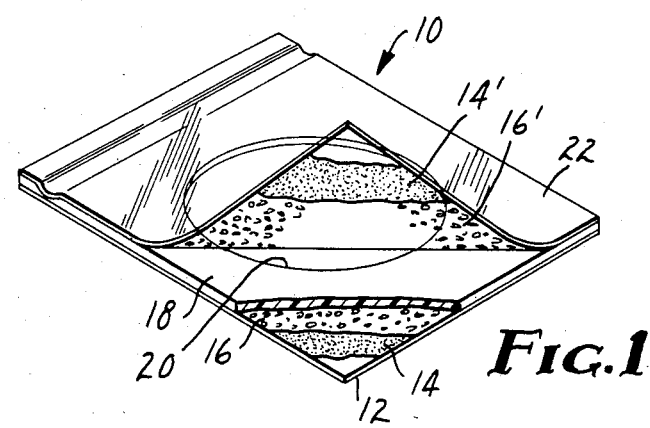
FIG. 1 is a top perspective view, partially in section, of a preferred microbiological growing device of the invention.

Substrate 12 is coated on its upper surface with a layer of an adhesive 14 which serves to hold the dry gelling agent and/or nutrients in a uniform monolayer for easy hydration. Adhesive 14 must be water-insoluble and non-inhibitory to the growth of microorganisms. Preferably, the adhesive is sufficiently transparent when wet to enable the viewing of bacterial colonies through the film coated with the adhesive. It is preferred that adhesive 14 be pressure-sensitive. However, heat-activated adhesives wherein a lower melting substance is coated onto a higher melting substance may also be used. Water-activated adhesives such as mucilage may also be useful.

Adhesive 14 should be coated onto substrate 12 in a thickness which is preferably less than the diameter of the particles of the powdered gelling agent and/or nutrients. The object is to apply enough adhesive to adhere the particles to the substrate but not so much that the particles become completely embedded in the adhesive. A uniform monolayer of powder 16 is desired with sufficient surface area exposed for hydration. Generally, an adhesive layer in the thickness range of 0.0002 to 0.0005 inch is suitable.

The presently preferred adhesive is a copolymer of isooctylacrylate/acrylamide (in a mole ratio of 94/6). Other pressure sensitive adhesives which may be used include isooctylacrylate/acrylic acid (in a mole ratio of 95/5 or 94/6) and silicone rubber. Adhesives which turn milky upon exposure to water are less preferred, but may be used in conjunction with a non-transparent substrate or where colony visualization is not required.

A monolayer of cold-water-soluble powder 16 is adhered uniformly to adhesive layer 14. Powder 16 comprises at least one ingredient selected from the group consisting of a gelling agent, one or more nutrients for growing microorganisms, and a mixture of a gelling agent and one or more nutrients for growing microorganisms. As used in the specification and claims, the term "powder" designates a finely divided particulate material having an average diameter of less than 400 micrometers. As used in the specification and claims, the term "cold-water-soluble" designates material which forms a solution in water at room temperature.

The "cold-water-solubility" of the powders employed in the devices of the present invention may result, for example, from the inclusion in these powders of an appropriate gelling agent. Suitable gelling agents for inclusion in powder 16 include both natural and synthetic gelling agents which form solutions in water at room temperature. Gelling agents such as hydroxyethyl cellulose, carboxymethyl cellulose, polyacrylamide, locust bean gum and algin form solutions in water at room temperature and are suitable gelling agents for providing powders which are "cold-water-soluble." The preferred gelling agents for powder 16 are guar gum and xanthan gum, these gelling agents being useful individually or in combination with one another. Nutrients for growing microorganisms form solutions in water at room temperature.

As indicated, powder 16 may comprise only a gelling agent. Where the device, as manufactured, contains a powder comprising only gelling agent, the end user adds his own special nutrients "tailored" to the type of microorganisms he wishes to grow. For example, dry powdered nutrients may be suspended in a rapidly-evaporating liquid such as ethanol or "Freon". In other instances, dry powdered nutrients may be suspended or dissolved in aqueous solutions. An aliquot of the liquid is added to the surface of substrate 12 which has been coated previously with adhesive and gelling agent. The liquid is allowed to evaporate, leaving ample nutrients along with the gelling agent.

In another embodiment of the invention, powder 16 may comprise nutrients but no gelling agent. Gelling agent is only required if one desires to visualize and/or isolate discrete bacteria colonies. In many microbiological tests, such as tests for bacteria identification or antibiotic susceptibility, broth media are used, and there is no need for a viscous gel. In devices for carrying out such tests, the gelling agent may be omitted.

Where gelling agent is included in powder 16, a sufficient amount of the gelling agent is adhered to the substrate so that a predetermined quantity of water or an aqueous sample, e.g., 1-3 milliliters, placed on the substrate will form a gel having a viscosity of about 1500 cps or more when measured at 60 rpm with a Brookfield Model LVF viscometer at 25° C. Gels of this viscosity will allow convenient handling and stacking and provide distinct colony identification. In most cases 0.025 to 0.050 gram of guar gum on a surface area of 3.14 sq. inches will provide a sufficiently viscous gel when hydrated with 1-3 milliliters of an aqueous sample. The size of the powder particles can be used to control the coating weight per unit area. For example, approximately 100 mesh guar gum coats to a weight of about 0.05 grams/2 inch diameter disc; and a 400 mesh guar gum coats to a weight of about 0.025 grams/2 inch diameter disc. If additional amounts of gelling agent and/or nutrients are required, the optional cover sheet of this embodiment may also be coated.

The preferred coating mixture for powder 16 is as follows:

15 grams guar gum or xanthan gum
5 grams peptone
2.5 grams yeast extract
1 gram dextrose
0.06 gram sodium carbonate
0.12 gram "Cab-O-Sil M-5" (a fumed silicon dioxide, commercially available from Cabot Corporation)

Sodium carbonate is employed to provide a medium exhibiting a neutral pH. "Cab-O-Sil M-5" is employed as a processing aid. Of course, the particular coating mixture used for powder 16 may depend upon the type of microorganisms to be grown.

In preparing a coating mixture comprising the above ingredients, the peptone, yeast extract, dextrose and sodium carbonate are dissolved in water and the resulting solution is spray-dried by conventional means to give a homogeneous mixture of the ingredients. The remaining ingredients are then combined with the above mixture to provide the final coating mixture.

It may be desirable to incorporate a dye into the medium mixture. Alternatively, the dye may be incorporated in adhesive 14. Suitable dyes are those which are metabolized by the growing microorganisms, and which cause the colonies to be colored for easier visualization. Examples of such dyes include triphenyl tetrazolium chloride, p-tolyl tetrazolium red, tetrazolium violet, veratryl tetrazolium blue and related dyes. Other suitable dyes are those sensitive to pH changes such as neutral red.

For some uses it may be desirable to form a medium stiff enough to allow inoculation of microorganisms by streaking. To form streakable medium, it may be desirable to include a small amount of cross-linking agent powder 16 where powder 16 includes a gelling agent. For example, with guar gum, cross-linking agents such as potassium tetraborate, aluminum or calcium salts may be added in an amount less than 1.0 percent by weight of powder 16. One must be careful to select a cross-linking agent which does not substantially affect the growth of the intended microorganism.

It is also contemplated within the scope of the invention that powder 16 may optionally include reagents necessary for carrying out certain microbiological tests. For example, antibiotics may be included for carrying out antibiotic susceptibility tests. For microorganism identification, reagents such as those which undergo a color change in the presence of a particular type of microorganism may be included.

In the device of FIG. 1, the body member includes a spacer element applied to the upper surface of substrate 12, the spacer element comprising a piece of spacer 18 having a circular hole 20 cut through the center to expose the particles 16 on substrate 12. The walls of hole 20 provide a well of predetermined size and shape to confine the medium following hydration. Spacer 18 should be thick enough to form a well of the desired volume, e.g., 1, 2 or 3 milliliter. Closed cell polyethylene foam is preferred material for spacer 18, but any material which is hydrophobic (non-wetting), inert to microorganisms, and capable of withstanding sterilization may be used.

Adhered to one edge of spacer 18 of the body member is a cover sheet 22. Cover sheet 22 is preferably transparent to facilitate counting of the bacterial colonies and is substantially impermeable to bacteria and water vapor. As used in the specification and claims, "substantially impermeable to bacteria and moisture vapor" designates cover sheets which prevent undesired contamination of the dehydrated medium during shipping, storage and use of the devices and which provide an environment which will support the growth of microorganisms during the incubation period. Generally, it will have the same properties as substrate 12, but need not be as stiff. Cover sheet 22 can be selected to provide the amount of oxygen transmission necessary for the type of microorganism desired to be grown. For example, polyester films have a low oxygen permeability (less than 5 g/100 in$^2$/24 hours per 0.001 inch of thickness) and would be suitable for growing anaerobic bacteria. On the other hand, polyethylene has a very high oxygen permeability (approximately 500 g/100 in$^2$/24 hours per 0.001 inch of thickness) and would be suitable for aerobic organisms. The presently preferred material for cover sheet 22 is a 1.6 mil biaxially-oriented polypropylene film. Cover sheet 22, as illustrated, is coated with optional layers of adhesive 14' and powder 16'. It is to be understood that cover sheet 22 may alternatively be adhered to substrate 12 of the body member and that it may be free of any coating or may be coated with a layer of pressure-sensitive adhesive only.

Figure 2:
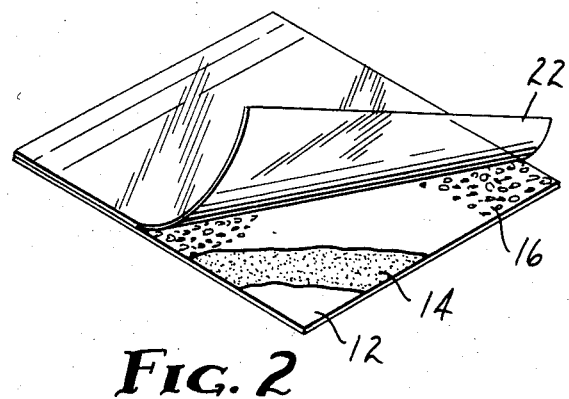
FIG. 2 is a top perspective view of an alternative embodiment of the invention.

The embodiment of FIG. 2 is identical to that of FIG. 1 except that spacer 18 is not present. A template, such as a weighted circular ring, may be applied temporarily to the outside of cover sheet 22, after closing, to confine the gel to a specific region.

Although both of the embodiments illustrated in the drawing have a cover sheet 22 attached to the device, it is also contemplated within the scope of the invention that the powder-containing embodiments may be uncovered and simply placed in a sterile environment during storage and incubation.

Another device (not illustrated) in accordance with the present invention comprises a bottom member comprising a self-supporting, water-proof substrate having upper and lower surfaces. Coated on at least a portion of the upper surfaces of the substrate is a coating which is substantially water-free and which consists essentially of a cold-water-reconstitutable material comprising at least one ingredient selected from the group consisting of a gelling agent, one or more nutrients for growing microorganisms, and a mixture of a gelling agent and one or more nutrients for growing microorganisms. As used in the specification and claims, the phrase "substantially water-free" designates a coating which has a water content no greater than about the water content of the dehydrated coating once it has been permitted to equilibrate with the ambient environment.

Suitable substrates for employment as the body member in this embodiment include those discussed above in connection with the illustrated embodiments.

This embodiment also comprises a cover sheet releasably adhered to at least a portion of the bottom member, the cover sheet being substantially impermeable to bacteria and water vapor. The cover sheet may be coated with a gelling agent and/or nutrient mixture in the form of, for example, the above-described cold-water-soluble powder adhered to the cover sheet by means of an adhesive layer or a coating such as that which is coated on the substrate of the body member in this embodiment. Alternatively, the cover sheet may also be coated with only a pressure-sensitive adhesive or may be free of any type of coating. Suitable materials for the cover sheet include those discussed above in connection with the illustrated embodiments.

The material employed in the coating of this embodiment is cold-water-reconstitutable. As used in the specification and claims, "cold-water-reconstitutable" designates material which forms a solution, sol or gel in water at room temperature. Suitable gelling agents for inclusion in the coating of this embodiment (if such are contained in the coating) include the above-described gelling agents which form solutions in water at room temperatures. In addition, it has been found that agar, after it has been dissolved in boiling water and deposited as a coating, is a material which is "cold-water-resonstitutible".

A preferred coating mixture for providing the coating of this embodiment is prepared by mixing the following ingredients:
15 grams agar
32.7 grams peptone
16.3 grams yeast extract
6.5 grams dextrose
2.0 grams "Guar M150" (a polysaccharide, commercially available from Celanese Corporation)
0.1 gram sodium carbonate
0.2 gram "Triton X-100" (a wetting agent, commercially available from Rohm and Haas)
1000 grams water The coating may optionally include dyes, antibiotics and cross-linking agents, examples of such ingredients including those described hereinabove.

The body member of this embodiment may optionally comprise a spacer element applied to the substrate, examples of suitable spacer elements including those discussed above in connection with the illustrated embodiments. In the event such a spacer element is present, the cover sheet may be, for example, releasably adhered to the spacer element.

Figure 3:
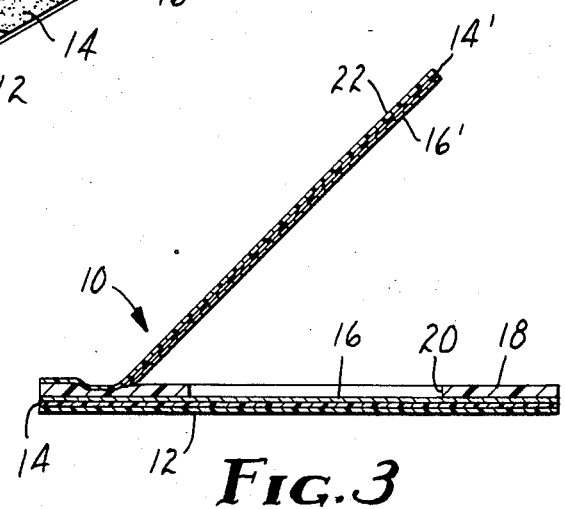
FIG. 3 is a cross sectional view of device of FIG. 1.
Figure 4:
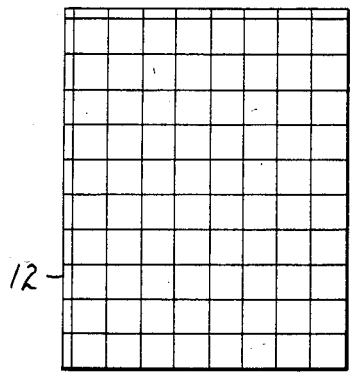
FIG. 4 is a top view of the device of FIG. 2 showing a grid pattern printed on the substrate.

The use of the devices of the present invention will be discussed with specific reference to the device of FIGS. 1 and 3. To use the device of FIGS. 1 and 3 as a pour plate, cover sheet 22 is pulled back and a predetermined quantity of water or an aqueous test sample is placed on substrate 12 of the body member. The gelling agent and/or nutrients adhered to substrate 12 by adhesive 14 are quickly hydrated or dissolved and a nutrient gel is formed. Cover sheet 22 is then replaced over the substrate, and a weighted plate placed on top to spread the sample completely. The device is then incubated for a predetermined period of time. Any bacterial colonies growing in the medium can be counted through the transparent cover film.

The device may also be conveniently used for "Rodac" testing wherein the surfaces of various objects are examined to determine the extent of bacterial contamination. Cover sheet 22 coated only with a pressure-sensitive adhesive is pulled back and touched to the surface being tested. The adhesive picks up any microorganisms from the surface being tested. The device is then hydrated, cover sheet 22 replaced, and the device incubated.

The invention may be further illustrated by reference to the following non-limiting examples. All parts are expressed as parts by weight unless otherwise indicated. The term "Standard Methods Nutrients" as used herein refers to the nutrient mixture described in Standard Methods for the Examination of Dairy Products, 14th Edition, American Public Health Association, Washington, D.C. It consists of 5 parts peptone, 2.5 parts yeast extract and 1 part dextrose.

EXAMPLE 1

Transparent polyester film (0.018 inch thick, "Scotchpar" from 3M Co.) is coated with IOA/acrylamide (in a mole ratio of 94/6) pressure-sensitive adhesive at a level (measured when dry) of 2 grains per 24 in$^2$ and dried. A "Volara" Type E polyethylene foam sheet (density: 6 lb/ft$^3$, from Voltek Inc., Lawrence, Mass.) (0.06 inch thick) having side dimensions of 3 and 3½ inches with a 2 inch diameter hole cut out of the center is adhered to the dried adhesive side of the above film. A mixture of 1 part Standard Methods Nutrients and 2 parts by weight guar gum powder HP-11 manufactured by Celanese Corp. is dusted on the adhesive-coated film exposed by the cut out and the excess shaken loose. A cover sheet consisting of 0.0016 inch transparent biaxially oriented corona-treated polypropylene film is coated with the same adhesive and coating weight used above, dried and dusted overall with a mixture of one part triphenyl tetrazoleum chloride and 1500 parts by weight of xantham gum ("Keltrol" from Kelco Company, Chicago, Ill.). The excess powder is shaken loose. The sheet is cut to a dimension of 3×3½ inches and placed on the previously made laminate with the powder sides facing each other. The cover sheet and body member are heat-sealed together at one edge. The device, consisting of the three layers, is sterilized in ethylene oxide. After suitable aeration the device is ready for use and will remain so with reasonable care in storage for many months.

For use, the device is placed on a level surface and the top sheet is lifted or removed. An aqueous test sample containing water (3 ml) is carefully placed in the center of the cut-out and the cover sheet replaced, powder side down. A slight weight may be applied to spread the liquid over the entire 2 inch cut-out. The device is placed in an incubator in the normal way. After incubation, the device is read for colony growth just as a normal pour plate. The bacteria are dyed red for easy quantitation.

EXAMPLE 2

A polyethylene-coated paper (0.0025 centimeter low density polyethylene on the top and bottom sides of a bleached kraft paper, density: 90 lb/320 yd$^2$ obtained from H. P. Smith) is printed with a 1 cm×1 cm black grid and a top varnish seal coat prior to the same adhesive coating of Example 1. A polystyrene foam sheet identified as Valcour EPS, 0.038 centimeter thick, 12 lbs/ft$^3$ density, is cut to $3 \times 3\frac{1}{2}$ inches with a 2 inch diameter cut-out, and adhered as in Example 1 in place of the polyethylene foam. The device is then powder coated, assembled and sterilized following the procedure of example 1. This device, when used, requires only a 1 ml water aliquot to hydrate and fill the 2 inch diameter cut-out. After incubation the number of colonies can be read by reflected, rather than transmitted, light. The grid aids in the making of an accurate count.

EXAMPLE 3-8

As indicated above, the preferred formulation of the dry medium of this invention uses guar gum, xantham gum and the Standard Methods Nutrients. Other cold-water-gelling agents may also be used. In the following examples, test samples of several gelling agents were made by mixing 1500 grams of each agent and 1 gram of triphenyl tetrazoleum chloride. The mixtures were then coated onto a polypropylene tape (dimensions: $3 \times 3\frac{1}{2}$ inches, 1.6 mils thick) coated with a pressure-sensitive adhesive of IOA/Acrylamide (in a mole ratio of 96/4) on one side. Mixing was done by hand. Coating was done by shaking an excess of powder on the tape and beating the excess off with a square rotating beater bar. These coated tapes were used as cover sheets. The bottom sheets were coated with adhesive, guar gum and nutrients as described in Example 2.

The devices were inoculated with bacterial isolates from raw milk. After incubation at 35° C., the plates were examined by standard techniques and the colonies counted. The results are tabulated in Table 1.

TABLE 1

| Example No. | Composition | 24 hr. Counts | 48 hr. Counts |
|---|---|---|---|
| 3 | Agar | 325 | 750 |
|  | Guar HP-11 (Celanese) | 250 | 700 |
| 4 | Guar CMHP (Celanese) | 250 | 320 |
| 5 | CMC 7H (Hercules) | 325 | 410 |
| 6 | Xanthan Gum (Kelco) | 450 | 700 |
| 7 | Kelco HV Alginate (Kelco) | 312 | 400 |
| 8 | Methocel 65HG (Dow) | 280 | 370 |
| Control | Pour Plate | 325 | 750 |

EXAMPLE 7

The established method of culturing used prior to the present invention uses agar gel in petri dishes. The following experiment compares this invention with the petri dish pour plate technique known as the Standard Methods procedure (Standard Methods for the Examination of Dairy Products, 14th Edition, American Public Health Association, Washington, D.C., pages 87–03).

In this experiment, 24 samples of raw milk (Dairy Quality Control Institute, 2353 Rice Street, St. Paul, Minn.) were tested using the device of this invention and the Standard Methods procedure. The device of the present invention contained guar gum/Standard Methods Nutrients in a 15/8 ratio by weight on the substrate and xantham gum/triphenyl tetrazolium chloride in a 1500/1 ratio on the cover sheet. The Standard Methods procedure utilizes Standard Methods Agar (BBL Co.).

The correlation coefficient between the results obtained using the present invention and the results obtained by the prior art procedure was 0.97. This test shows that the present invention provides increased efficiency and convenience without sacrificing accuracy.

EXAMPLE 10

This experiment was done in a similar manner as in 9 above, except that different bacteria suspensions were used in place of standard milk samples. The bacteria inoculant suspensions had a concentration of approximately $1 \times 10^2$ CFU/ml (colony forming units per milliliter). The standard pour plate test was run according to the Standard Methods procedure (Standard Methods for the Examination of Dairy Products, American Public Health Association, pages 87–93). Results are in Table II.

TABLE II

| Bacteria | This Invention CFU/ml | CFU/ml Standard Methods Procedure |
|---|---|---|
| Salmonella | 220 | 300 |
| E. Coli | 35 | 17 |
| Klebsiella | 55 | 9 |
| S. aureus | 80 | 85 |
| Pseudomonas | 120 | 350 |
| S. epidermidis | 155 | 220 |
| B. subtilis | 1 | 1 |
| S. marcescens | 340 | 250 |
| Shigella | 13 | 15 |
| S. pyogenes | 15 | 16 |
| E. cloacae | 32 | 35 |

EXAMPLE 11

Transparent, corona treated, biaxially-oriented polypropylene film (0.0016 inch thick) was coated with IOA/acrylamide (in a mole ratio of 94/6) pressure-sensitive adhesive at a level (measured when dry) of 2 grains per 24 in$^2$ and the adhesive layer was dried. The pressure-sensitive adhesive also contained 0.0006 grams of 2,3,5-triphenyl tetrazolium chloride per gram of dry adhesive. "Guar Meyprogat 150" (a polysaccharide commercially available from Celanese) was dusted on the adhesive-coated film at a level of 6 grains per 24 in$^2$. Onto the layer of powder was coated a 20% solids solution of Standard Methods Nutrients broth, the broth being dried to provide a coating weight of 2 grains per 24 in$^2$.

Devices were prepared using sheets of this material as both the bottom member and the cover sheet. The devices were inoculated with 1 cc. of appropriate dilutions of bacteria and incubated 48 hours at 32° C. Results were compared to the results observed using the standard methods procedure, the results appearing in Table III below:

TABLE III

| Bacteria | The Device of this Example CFU/ml | CFU/ml Standard Methods Procedure |
|---|---|---|
| E. coli | 153 | 120 |
| S. aureus | 71 | 131 |
| S. fecalis | 129 | 107 |

EXAMPLE 12

"Schoeller Type MIL" photoprint paper (commercially available from Schoeller Pulaski) was coated at a level of 3 grains per 24 in² (measured when dry) with the following solution and dried:

| Coating Solution | |
|---|---|
| Ingredient | Grams |
| Agar | 15 |
| Peptone | 32.7 |
| Yeast Extract | 16.3 |
| Dextrose | 6.5 |
| "Guar Meyprogat 150" | 2.0 |
| Water | 1000 |

The coated photoprint paper forms the bottom member of the device.

The cover sheet is a powder-coated polypropylene film of the type described in Example 11 above except that here the pressure-sensitive adhesive comprises 0.0012 grams of 2,3,5-triphenyl tetrazolium chloride per gram of dry adhesive.

The devices were inoculated with 1 cc. of appropriate dilutions of the bacterial cultures indicated in Table IV below. Results after 48 hours incubation at 32° C. were as indicated in Table IV below. Results are also included for the Standard Methods Procedure.

TABLE IV

| Bacteria | The Device of this Invention CFU/ml | CFU/ml Standard Methods Procedure |
|---|---|---|
| S. aureus | 330 | 335 |
| P. fragi | 128 | 275 |
| S. fecalis | 111 | 116 |
| S. agalactiae | 180 | 170 |
| S. cremoris | 900$^a$ | 900$^a$ |
| E. coli | 143 | 177 |
| B. subtilis | 11 | 20 |
| Pseudomonas | 120 | 130 |

$^a$number of colonies estimated due to large number thereof.

When the devices of this Example were inoculated with Examples of raw milk, a 0.934 correlation coefficient was observed relative to standard agar plates which were similarly inoculated.

EXAMPLE 13

"Schoeller Type MIL" photoprint paper was coated at a level of 3 grains per 24 in² (measured when dry) with the following solution and dried:

| Coating Solution | |
|---|---|
| Ingredient | Grams |
| Peptone | 90 |
| Yeast Extract | 45 |
| Dextrose | 18 |
| "Guar M150" | 8 |
| Sodium Carbonate | 0.7 |
| "Triton X-100" (a wetting agent, commercially available from Rohm and Haas Corp.) | 0.2 |
| Water | 1000 |

The coated photoprint paper forms the bottom member of the device.

The cover sheet was the same as that employed as the cover sheet in Example 12.

The devices were inoculated with 1 cc. of appropriate dilutions of the bacterial cultures indicated in Table V below. Results after 48 hours incubation at 32° C. were as indicated in Table V below. Results are also included for the Standard Methods Procedure.

TABLE V

| Bacteria | The Device of this Invention CFU/ml | CFU/ml Standard Methods Procedure |
|---|---|---|
| S. aureus | 30 | 30 |
| P. fragi | 57 | 95 |
| S. fecalis | 100 | 95 |
| S. agalactiae | 83 | 67 |
| S. cremoris | 104 | 101 |
| E. coli | 8 | 6 |
| B. subtilis | 165 | 195 |

EXAMPLE 14

A device in accordance with the present invention was constructed which consisted of the coated photoprint paper of Example 12 as the bottom member. The cover sheet consisted of a transparent, corona treated, biaxially-oriented polypropylene film (0.0016 inch thick) which had been coated with IOA/acrylamide (in a mole ratio of 94/6) pressure-sensitive adhesive at a level (measured when dry) of 2 grains per 24 in². The pressure-sensitive adhesive also contained 0.0012 grams of 2,3,5-triphenyl tetrazolium chloride per gram of dry adhesive.

After inoculating the device of this Example with a 0.1 cc of a dilution of E. Coli and incubating 24 hours, individual colonies were observed.

What is claimed is:

1. A device for growing microorganisms, comprising: a body member comprising a self-supporting, waterproof substrate having upper and lower surfaces; a layer of adhesive-coated on said upper surface of said substrate, said adhesive being non-inhibitory to the growth of microorganisms; and a cold-water-soluble powder adhered uniformly to said adhesive, said powder comprising at least one ingredient selected from the group consisting of a gelling agent, one or more nutrients for growing microorganisms, and a mixture thereof; said device being free of matrixes which adversely affect visualization and isolation of bacterial colonies.

2. The device according to claim 1, further comprising a cover sheet releasably adhered to at least a portion of said body member.

3. The device according to claim 2, wherein said cover sheet comprises a transparent film.

4. The device according to claim 3, wherein said film is selected from the group consisting of polyester, polyethylene, polypropylene, polystyrene and silicone.

5. The device according to claim 1, wherein said powder comprises a gelling agent in sufficient amount to provide a gel having a Brookfield viscosity of at least 1500 cps when hydrated with a predetermined amount of water.

6. The device according to claim 1, further comprising a hydrophobic spacer element adhered to said upper surface of said substrate forming side walls to retain a predetermined amount of liquid in contact with said substrate.

7. The device according to claim 6, wherein said spacer element comprises a hydrophobic foam sheet having a hole therein.

8. The device according to claim 7, wherein said foam is polystyrene or polyethylene.

9. The device according to claim 1, wherein said substrate is a film selected from the group consisting of polyester, polypropylene, polyethylene and polystyrene.

10. The device according to claim 9, wherein said film is about 0.001 to 0.015 inch thick.

11. The device according to claim 1, wherein said substrate has a grid pattern printed thereon.

12. The device according to claim 1, wherein said powder comprises one or more nutrients for growing microorganisms.

13. The device according to claim 1, wherein said powder comprises a gelling agent and one or more nutrients for growing microorganisms.

14. The device according to claim 1, wherein said gelling agent is selected from the group consisting of xanthum gum, guar gum, carboxymethyl cellulose, hydroxyethyl cellulose, and algin.

15. The device according to claim 14, wherein said gelling agent is guar gum, xanthum gum or mixtures thereof.

16. The device according to claim 1, wherein said adhesive is a pressure-sensitive adhesive.

17. The device according to claim 16, wherein said adhesive is substantially transparent when wetted with water.

18. The device according to claim 17, wherein said adhesive is a copolymer of isooctyl acrylate and acrylamide in a mole ratio of 94:6, respectively.

19. The device according to claim 1, wherein one of said powder and said adhesive contains a dye which is metabolizable by microorganisms and which causes said microorganisms to be colored or fluorescent.

20. The device according to claim 19, wherein said dye is selected from the group consisting of triphenyltetrazolium chloride, p-tolyltetrazolium red, tetrazolium violet and veratryltetrazoleum blue.

21. A device for growing microorganisms, comprising: a bottom member comprising a self-supporting water-proof substrate having upper and lower surfaces with a coating adhered to at least a portion of said upper surface, said coating being substantially water-free and consisting essentially of a cold-water-reconstitutable material comprising at least one ingredient selected from the group consisting of a gelling agent, one or more nutrients for growing microorganisms, and a mixture thereof; and a cover sheet releasably adhered to at least a portion of said bottom member and capable of substantially overlying said coating on said substrate, said cover sheet being substantially impermeable to bacteria and water vapor and having a coating adhered to at least a portion of the surface of said cover sheet facing said body member, said coating being substantially water-free and consisting essentially of a water-reconstitutable material comprising at least one ingredient selected from the group consisting of a gelling agent, one or more nutrients for growing microorganisms, and a mixture thereof; said device being free of matrixes which adversely affect visualization and isolation of bacterial colonies.

22. The device according to claim 21, wherein said coating on said cover sheet consists essentially of a cold-water-soluble powder adhered to said cover sheet by means of an adhesive, said adhesive being coated on said substrate and being non-inhibitory to the growth of microorganisms, and said cold-water-soluble powder being adhered uniformly to said adhesive.

23. The device according to claim 22, wherein said coating on said substrate consists essentially of a cold-water-soluble powder adhered to said substrate by means of an adhesive, said adhesive being coated on said substrate and being non-inhibitory to the growth of microorganisms, and said cold-water-soluble powder being adhered uniformly to said adhesive.

24. The device according to claim 23, wherein said cold-water-soluble powder adhered to said substrate comprises a gelling agent and one or more nutrients for growing microorganisms, and said cold-water-soluble powder adhered to said cover sheet comprises a gelling agent.

25. The device according to claim 23, wherein said adhesive-coating on said substrate and said adhesive-coated on said cover sheet are both pressure-sensitive adhesives.

26. The device according to claim 22, wherein said coating on said substrate comprises a gelling agent and one or more nutrients for growing microorganisms, and said cold-water-soluble powder adhered to said cover sheet comprises a gelling agent.

27. The device according to claim 22, further comprising a hydrophobic spacer element adhered to said upper surface of said substrate forming side walls to retain a predetermined amount of liquid in contact with said substrate.

28. The device according to claim 22, wherein said adhesive is a pressure-sensitive adhesive.

29. The device according to claim 21, further comprising a hydrophobic spacer element adhered to said upper surface of said substrate forming side walls to retain a predetermined amount of liquid in contact with said substrate.

30. The device according to claim 21, wherein said coating comprises a gelling agent selected from the group consisting of xanthum gum, quar gum, carboxymethyl cellulose, hydroxyethyl cellulose and algin.

31. The device according to claim 21, wherein said coating comprises a gelling agent selected from guar gum, xanthum gum and mixtures thereof.

32. The device according to claim 21, wherein said substrate is selected from the group consisting of a polyester film, polypropylene film, polyethylene film, polystyrene film, and polyethylene-coated paper.

33. The device according to claim 21, wherein said substrate is selected from the group consisting of a film and a paper which has a water-proof coating thereon, and said cover sheet is a film.

* * * * *